(12) United States Patent
Assaker et al.

(10) Patent No.: US 8,715,175 B2
(45) Date of Patent: May 6, 2014

(54) THORACIC RETRACTOR

(75) Inventors: Richard Assaker, Kain (BE); Yann Thouement, Les essarts le roi (FR); Regis Besse, Guyancourt (FR)

(73) Assignee: Karl Storz GmbH & Co. KG (DE)

(*) Notice: Subject to any disclaimer, the term of this patent is extended or adjusted under 35 U.S.C. 154(b) by 280 days.

(21) Appl. No.: 13/157,067

(22) Filed: Jun. 9, 2011

(65) Prior Publication Data
US 2012/0022335 A1 Jan. 26, 2012

(30) Foreign Application Priority Data
Jun. 9, 2010 (EP) .................................... 10005960

(51) Int. Cl.
*A61B 1/32* (2006.01)

(52) U.S. Cl.
USPC .......................................................... 600/225

(58) Field of Classification Search
USPC .......................................... 600/201–227, 232
See application file for complete search history.

(56) References Cited

U.S. PATENT DOCUMENTS

| 5,299,563 | A | * | 4/1994 | Seton ............................ 600/215 |
| 5,365,921 | A | | 11/1994 | Bookwalter et al. |
| 6,371,911 | B1 | * | 4/2002 | Hossain et al. ............... 600/232 |
| 6,620,097 | B1 | | 9/2003 | Bookwalter et al. |
| 2002/0177753 | A1 | | 11/2002 | Dobrovolny |
| 2004/0059192 | A1 | | 3/2004 | Cartier et al. |
| 2004/0193018 | A1 | | 9/2004 | Thalgott et al. |
| 2009/0254187 | A1 | | 10/2009 | Bjork |

FOREIGN PATENT DOCUMENTS

| DE | 20003335 U1 | 7/2000 |
| EP | 0411586 A1 | 2/1991 |
| FR | 1019217 A | 1/1953 |

OTHER PUBLICATIONS

International Search Report; Application No. EP 10 00 5960; Sep. 16, 2010; 8 pages.

* cited by examiner

*Primary Examiner* — Mary Hoffman
*Assistant Examiner* — Tara Carter
(74) *Attorney, Agent, or Firm* — St. Onge Steward Johnston & Reens LLC

(57) ABSTRACT

A surgical retractor has a rail, a first arm protruding from the rail at an angle, a second arm being movably mounted on the rail and extending substantially parallel to the first arm, and a multiplicity of holding elements mounted on the first and second arms. A holding element has a multi-axis joint for pivotably holding a blade for engaging tissue to be retracted. In this way, a most flexible surgical retractor is provided.

15 Claims, 7 Drawing Sheets

THORACIC RETRACTOR

CROSS-REFERENCE TO RELATED APPLICATIONS

The present application claims priority of European patent application No. 10005960.9 filed on Jun. 9, 2010, the content of which is incorporated herein by reference.

FIELD OF THE INVENTION

The present invention relates to a surgical retractor for performing surgical interventions, in particular heart, thorax or spinal surgical interventions.

BACKGROUND OF THE INVENTION

In surgical interventions, it is frequently required to spread tissue in order to provide access to body structures situated below the tissue to be spread. In particular, in many heart, thorax and spinal surgeries, the sternum is divided longitudinally; the two parts of the sternum are then spread from each other, thus opening up the thorax in order to enable the surgeon to perform surgery inside or through the chest cavity.

For spreading and holding tissue, surgical retractors are employed. Such a retractor usually comprises at least two tissue holding members and a support structure. The tissue holding members are designed for engaging with the tissue, in particular with the edges created by dividing the tissue, and are arranged in an opposing relationship on the support structure. The support structure serves to support the tissue holding members and comprises a drive mechanism for spreading the opposing tissue holding members from each other in order to spread the tissue edges from each other. In use, the support structure may be placed on the body surface, with the tissue holding members extending into the body and into the cavity to be kept open.

A particular retractor for performing heart and thorax surgeries is disclosed in DE 200 03 335 U1. The known retractor comprises a rail, a first arm protruding from the rail at an angle and a second arm extending approximately parallel to the first arm. The arms are equipped with blades for insertion into a cavity and for holding tissues on both sides of the cavity. The blades extend in a direction substantially transverse to the arms and to the rail. The distance between the two arms can be modified in order to spread the tissues, providing space for performing a surgical intervention.

According to DE 200 03 335 U1, the blades are pivotably mounted within a blade holder, the blade holder being freely movable along a respective arm. When the blades are engaged with tissue, the blade holder is blocked against movement along the arm by the counter-force exerted by the tissue on the blade. In this way, the positions of the blades can be easily adjusted to a particular surgical situation.

However, the tissues to be spread may not always be adequately held by blades which extend perpendicular or transverse to the directions of the holding arms and the rail. While such blades may be optimal in one surgical situation, it may be necessary to exert a holding force in a different direction on a particular piece of tissue in another situation. Such a situation may arise during a surgical intervention in a foreseeable or in a not foreseeable manner. The requirement of an obliquely directed holding force may arise, e.g., also due to lifting one side of the tissue for better accessing or viewing organs on that side.

SUMMARY OF THE INVENTION

Therefore, it is an object of the present invention to provide a surgical retractor which is more flexibly adaptable to a variety of surgical situations and/or types of surgical procedures.

This object is met by a surgical retractor according to claim 1. Particular embodiments of the present invention are indicated in the dependent claims.

In accordance with claim 1, a surgical retractor comprises an elongate rail or crossbar. The rail or crossbar may be formed by a straight rod, which may be equipped with a row of teeth to be engaged by a spreading mechanism. The retractor further comprises a first holding arm protruding from the rail at an angle, in particular at an angle of approximately 90°. The first arm may be integral with the rail or may be releasably mounted on the rail. The retractor further comprises a second arm, which, as the first arm, may be formed by an elongate rod. The rods of the first and second arms may have approximately the same lengths and cross-sections. The second arm is mounted on the rail such that it is movable with respect to the rail and extends substantially parallel to the first arm. For this purpose, the second arm may comprise a mounting block to which the rod of the second arm is fixed, and which is mounted movably on the rail. The mounting block may include a spreading mechanism for moving the second arm relative to the rail and in a substantially parallel manner relative to the first arm, thus permitting modification or adjustment of the separation between both arms. The mounting block may be mounted releasably on the rail. The rail and the first and second arms may comprise further members, such as, e.g., mounting means for mounting further surgical devices, or stopping means for limiting the usable portions of the rail or the arms.

The retractor further comprises a multiplicity of holding elements which are mounted or mountable on the first and second arms. If the rods of the arms have different cross-sections, the holding elements may be specific to each of the arms. However, for simplicity, flexibility and ease of use, it is preferred that the rods of the arms have equal cross-sections, such that the holding elements can be arbitrarily mounted on either arm. At least one or each of the holding elements comprises a joint for pivotably or rotatably holding at least one blade for engaging tissue to be retracted. Thus, when a holding element is mounted on one of the arms, a blade can be held by the holding element in such a position as to engage with the tissue that is to be spread or retracted. The blade is held pivotably by the joint in order to better accommodate the tissue to be retracted. In particular, when the pivot axis is perpendicular to a longitudinal axis of the arm on which the holding element is mounted, the blade can be rotated by the surgeon in such a way that the surface of the blade roughly coincides with the surface of the tissue to be held or spread.

According to the present invention, the joint is a multi-axis joint permitting rotation of the blade with respect to the holding element about at least two axes. In particular, the multi-axis joint permits pivoting or swiveling the blade about two axes which are perpendicular upon each other. One or both axes may be transverse to a longitudinal axis of the arm on which the holding element is mounted. Thus, if the blade has an elongate shape with a blade axis, rotation about that axis may be enabled as well as swiveling about an axis perpendicular to the blade axis. The multi-axis joint may be, e.g., a knuckle joint or universal joint.

Therefore, due to the rotation of the blade about at least two axes, an improved adaptation of the retractor to various surgical situations can be achieved.

The blade may be held by the holding element in a detachable or in a non-detachable manner. Thus, e.g., it may be possible to connect or disconnect the multi-axis joint and thus to connect or disconnect a blade to the retractor. Alternatively, the joint may present a non-releasable connection connecting the blade in a non-releasable manner to a body of the holding element.

In a preferred embodiment of the present invention, the holding element comprises at least one blade holder for releasably holding at least one blade. The holding element further comprises a holding element body for connecting the holding element to an arm. The blade holder is connected by the two-axis joint, which preferably is not releasable, to the holding element body. A set of blades of various kinds or lengths may be provided to suit requirements in a variety of surgical situations, the different blades fitting into one or each blade holder.

In this way it is possible to exchange blades during a surgical procedure without removing the holding element from the arm. In particular, a blade can be removed from a blade holder and a different blade can be inserted into the blade holder without removing the holding element from the arm, and without moving or removing other holding elements. Thus, a further improvement in flexibility of application of the retractor is achieved.

According to a further preferred embodiment of the invention, a blade can be freely inserted into the blade holder, so that it is in a position for engaging issue to be retracted. The blade can be fixed within the blade holder by the counter-force exerted by the retracted tissue on the blade. For this purpose, the blade holder may be provided in the shape of a bracket or a ring with sufficient clearance such that the blade can be inserted freely but gets wedged in or tilted and thus is blocked if a lateral force acts upon its distal end. The bracket or ring and/or the blade may be provided with surfaces for increasing friction, such as a rough surface or a coating. The blade may exhibit projections for blocking movement within the blade holder when a lateral force acts upon its distal end to slightly tilt the blade within the bracket or ring. In particular, the blade may be height-adjustable by inserting into the blade holder to a desired depth, being fixed in that position in the blade holder by the lateral force exerted by the tissue.

By freely inserting the blade, the blade being automatically fixed within the blade holder when the blade is engaged with tissue, the retractor can be most easily adapted by a surgeon to current requirements within a surgical operation.

Alternatively, fixation means can be provided for fixing a blade to the blade holder, such as a screw, an elastic bracket or the like. In this way, a most secure fixation of the blade can be achieved.

The blades may exhibit an elongate shape with a proximal and a distal section. The proximal section may comprise a head for gripping and handling the blade, which may also act as a stop when the blade is inserted into the blade holder. The distal section is designed for engaging the tissue. For this purpose, it may exhibit a flattened side, which may be structured in order to increase friction and to avoid slipping of the tissue. In particular, the flattened surface of the distal section may comprise ribs which are directed substantially transverse to a longitudinal blade axis. The blade may also comprise longitudinal ribs for reinforcing the blade, permitting a larger force to be exerted and avoiding bending of the blade.

The blades may be provided in various lengths, widths and/or shapes, for accommodating the various tissue retraction requirements encountered during surgical operations. Preferably, several or all kinds of the blades fit into each blade holder, thus providing a modular system for increased flexibility. In particular, it may be possible to employ the same retractor for adult as well as for pediatric operations, as well as for various types of surgical procedures.

The blades are generally designed to avoid trauma when holding the tissue, in particular to protect the intercostal nerves during heart, thorax or spinal surgery. In particular, the blades may be shaped without sharp edges, at least in their distal sections.

While the rail, the arms and most parts of the holding elements preferably are made of steel, in particular of stainless steel, the blades may consist of a plastic material or be coated with such a material. Thus, the blades may be designed as single-use instruments, while the retractor generally is a re-usable instrument.

According to a preferred embodiment of the surgical retractor, the multi-axis joint is a spherical joint for providing three rotational degrees of freedom for the retractor blade. A spherical joint may, in particular, be a ball-and-socket joint consisting of a convex spherical surface enclosed by a concave socket. The socket may be fixed to or formed by the body of the holding element, while the convex spherical surface may be connected by a stud to the blade holder. However, a spherical joint may be equivalently formed by a combination of other joints, e.g., by a combination of a multiplicity of one-axis hinges, or by a knuckle or universal joint with an additional axial degree of freedom.

By employing a spherical joint for holding a blade, the blade can be rotated with respect to its longitudinal axis as well as inclined in any direction. In this way, the retractor can be adjusted to any tissue retraction requirements arising during a surgical intervention. Thus, the retractor can be employed in surgical procedures in a particularly easy and flexible manner.

Having been rotated into a particular orientation, the blade may be held in that orientation by friction within the multi-axis joint and/or by a self-blocking or ratchet mechanism which permits fixation of the blade in a multiplicity of orientations and which may be operated by a counter-force of the tissue retracted.

Alternatively or additionally, according to a preferred embodiment of the invention, the holding element comprises fixation means for blocking at least one of the axes of the multi-axis joint, i.e. for inhibiting rotational movement about the respective axis of the joint. Preferably, the fixation means act to block all rotational degrees of freedom of the blade with respect to the holding element. Most preferably, a single actuation element is provided for blocking all rotational degrees of freedom of the blade.

Therefore, a blade can be adjusted according to any current surgical requirements by rotating the blade, and then fixed in the corresponding rotational position. In particular, the blade can be moved by the surgeon by hand and then fixed in the desired orientation by actuating an actuation element of the fixation means. This provides for a particularly easy and flexible operation of the retractor.

Moreover it is preferred that the fixation means comprises a fixation screw acting upon a movable member of the multi-axis joint. Such a movable member may be, in particular, a shaft of a multi-axis hinge, or the ball of a ball-and-socket joint. When the holding element comprises a body, a blade holder being connected by the multi-axis joint to the body, the fixation screw may be arranged on the body, acting upon a member of the joint movable relative to the body, or the fixation screw may be arranged on the blade holder, acting upon a member of the joint movable relative to the blade holder. Preferably, as the holding element generally has a constant orientation with respect to the arm on which it is mounted, the fixation screw is situated on the holding element body. The fixation screw acts to block the rotational movement by engaging with the surface of the movable member or by pressing the movable member against its seat. The fixation screw may act directly or indirectly upon the movable member, thus, e.g., an intermediate element may be provided for avoiding torque transfer.

In this way, the blade can be easily pivoted into any orientation desired by the surgeon and then fixed in that orientation. The screw employed for this purpose enables the surgeon to readily exert a sufficient amount of force to lock the blade firmly so that it can be employed for retracting tissue. Therefore, the retractor exhibits both flexibility and stiffness.

If the multi-axis joint is a ball-and-socket joint, the fixation screw may, in particular, operate upon the surface of the ball to block rotation of the ball with respect to the socket. In this way, the three rotational degrees of freedom provided by a spherical joint can be blocked by tightening a single fixation screw and, inversely, can be released by loosening the fixation screw. Thus, adjustment of the surgical retractor is made particularly simple.

According to a further preferred embodiment of the present invention, the holding element comprises an aperture or opening into which a rod of an arm can be inserted for mounting the holding element on the arm, and the holding element comprises fixation means for fixing the holding element on the arm. The aperture may be a hole or a recess in a body of the holding element, the shape of which roughly matches with the cross-section of the rod. In particular, the holding element may be movable along the rod in order to adjust the position of a blade held by the holding element. Fixation means are provided for fixing the holding element on the arm, i.e., at least for blocking a translational movement of the holding element along the rod. This permits a particularly secure fixation of the holding elements with respect to the retractor frame. Preferably, the holding element can be locked in any desired position on the arm.

In a preferred embodiment, the opening or aperture is a recess in the holding element for laterally inserting a rod of an arm. In particular, a body of the holding element may be designed as an open frame, into which the rod can be inserted from the open side. In this way, a holding element can be placed on an arm without inserting the rod from one its ends. This presents a particular advantage if it turns out during a surgical procedure that an additional holding element is required and has to be placed between other holding or functional elements already mounted on the respective arm.

The fixation means for fixing the holding element on the arm may serve to hold the holding element in a movable manner on the arm as well as to lock the holding element with respect to a translational movement along the arm. In this way, the particular advantage is achieved that the surgeon can mount and block an additional holding element on the arm with the same fixation means, thus further simplifying operation and increasing flexibility of the retractor.

In a preferred embodiment of the invention, the fixation means for fixing the holding element on the arm comprises a fixation screw which is situated on a first side of the aperture to act upon a first surface of the rod. When the holding element is mounted on an arm of the retractor and therefore a rod is present in the aperture, the fixation screw can therefore be operated to press upon one of the surfaces of the rod, thus locking the holding element against translational movement along the rod. This permits the holding element to be easily shifted into any desired position and fixed in that position on the arm by tightening the fixation screw.

In a particularly preferred embodiment, a body of the holding element is configured as an open frame, and the fixation screw can be operated into a first position permitting placement of the holding element on the rod. Thus, in the first position of the fixation screw, the rod can be laterally inserted into the recess of the body of the holding element. In a second position of the fixation screw, the holding element is held on the rod, i.e., lateral extraction of the rod out of the aperture is inhibited, but translational movement of the holding element along the rod is still enabled. When the fixation screw is turned into a third position, any kind of movement of the holding element relative to the rod is inhibited. In this way, the fixation element permits a stepwise procedure of mounting, shifting and fixing the holding element on the arm, which provides for a particularly convenient and easy operation of the retractor.

According to a further particularly preferred embodiment, a movable member of the multi-axis joint is arranged on a second side of the opening or aperture of the holding element, such that a second surface of the rod can be pressed against a surface of the movable member of the multi-axis joint by operating the fixation screw. Thus, by tightening the fixation screw, the multi-axis joint and the rod can be clamped against each other within the holding element, effectively locking the blade in a given orientation and at the same time locking the holding element at a given position on the arm.

In this way, the surgeon is enabled to fix both the blade with respect to the holding element and the holding element with respect to the arm by tightening only one fixation screw. If a blade is to be re-oriented and/or moved in a direction along the respective arm of the retractor, thus only one single screw needs to be loosened for making the blade freely movable, and only that same single screw needs to be tightened for fixing the blade with respect to all rotational degrees of freedom and the and translational degree of freedom permitted. This is a considerable advantage in handling the retractor in surgical operations.

Alternatively, the fixation screw may be arranged between the multi-axis hinge and the rod to press, e.g., upon a wedge between the movable member of the multi-axis hinge and the rod. Thus, when the fixation screw is tightened, the joint is locked by pressing the movable member against a bearing surface of the joint, and the holding element is locked on the rod by pressing the rod against the first side of the aperture of the holding element. Thus, in a similar way, the fixation screw can be employed for locking the blade with respect to the rotational degrees of freedom and at the same time locking the holding element with respect to translation along the arm.

In a further preferred embodiment, the movable member is the ball of a ball-and-socket joint and the socket is connected to the holding element, preferably rigidly connected to the body of the holding element. In this configuration, by tightening the fixation screw the ball is pressed between the socket and the rod, and the rod is pressed between the ball and the fixation screw. The fixation screw may operate directly or indirectly on the rod surface. Thus, e.g., an intermediate member between the rod and the screw may be provided in order to inhibit torque transfer, and/or an intermediate member may be provided between rod and ball for inhibiting play transverse to the direction of force transfer. The surfaces being pressed against each other may be provided with a defined roughness or may be coated in order to increase friction and to improve fixation. The surfaces may be hardened in order to avoid the formation of notches when a high amount of force is exerted.

A surgical retractor of this kind is able to hold the blades firmly to exert sufficient force on the tissue, and is very easy to operate. Moreover, the retractor can be provided in smaller or larger sizes, and even a relatively small-sized retractor permitting considerable force to be exerted on the tissue to be retracted. Thus, the retractor is suitable for a large variety of types of surgical operations. The simple design has the further advantage of permitting easy cleaning and sterilization.

In order to improve stiffness, a rod of an arm of the retractor may have a generally rectangular cross-section. The first and second surfaces of the rod may be surfaces opposing each other. In this way, a direct force transfer for efficient clamping and locking the rod against the joint within the holding element can be achieved. The first and second surfaces may, however, be inclined with respect to each other and/or comprise a shape deviating from a flat surface.

In particular, in a surgical retractor according to a further preferred embodiment a rod exhibits a second surface which is concave such that the rod can be held within the recess by the ball engaging the concave surface. Preferably, the second surface exhibits a cylindrical groove, the cylindrical groove extending along a longitudinal direction of the rod. Most preferably, the radius of the cylindrical surface approximately equals the radius of the ball of the joint, so that by pressing the rod against the ball a line of contact is formed between the second surface and the ball. In this way, a particularly rigid configuration is achieved.

In further preferred embodiments, which are independent of the function of the fixation screw for locking the blade rotation and/or for locking the holding element translation, the fixation screw is arranged in the holding element in such a manner that a longitudinal axis of the fixation screw is oblique with respect to a plane formed by the arm and the rail in a portion adjacent to the arm. As in many operations the retractor frame is put flat on the patient's body, the plane defined by the arms and the rail or at least by portions of an arm and a rail frequently roughly corresponds to the surface of the body. By arranging the longitudinal axis of the fixation screw oblique to that plane, free operation of the screw by the surgeon is enabled without any obstruction by the body of the patient or other surgical devices. The fixation screws may be operable by hand or with a particular tool, such as a screwdriver.

Preferably, the fixation screws of the holding elements mounted on the first arm extend in a direction away from the second arm, and vice versa. In this way, obstruction by the respective other arm of the retractor is avoided.

If the rod of the arm has flat lower and upper surfaces, the body of the holding element extends substantially in a plane parallel to the lower and upper surfaces, and the force for clamping the multi-axis joint against the rod will act essentially in the same plane. If the fixation screw has a direction oblique to that plane, a force component perpendicular to the plane can be created which serves to press further surfaces of the rod against the body of the holding element. In this way, stability will be further increased.

The first surface of the rod, or at least a section of the first surface, preferably is substantially perpendicular to the axis of the fixation screw, thus permitting a sufficient amount of force to be transmitted on the rod. Thus, if the longitudinal direction of the fixation screw is oblique with respect to the direction of force transfer to the second side of the rod, at least a part of the first side of the rod is also oblique to that direction.

Preferably, the tip of the fixation screw acting upon the first surface forms a substantially flat or hollow surface. Thus, when the fixation screw is tightened, the tip makes more than a point contact with the first surface of the rod, the enlarged contact surface further enhancing stability. This effect may as well be achieved by an intermediate member arranged between the fixation screw and the first surface of the rod.

The surgical retractor according to the present invention may be equipped with further functional elements, which may be mountable on the first and/or second arms. Such a further functional element may be, e.g., an illumination device for illuminating the cavity or the surgical site in order to further improve the surgeon's view.

An illumination device may comprise a light guide and a light guide holding element. The light guide may be connectable to an external light source and can be adjusted to direct the light transmitted from the external light source into the cavity held open by the retractor, in particular to a desired site within the cavity. The light guide holding element may be configured in a similar way as the holding elements described above for holding the blades. In particular, the light guide holding element may be configured as an open frame which can be mounted on one of the arms without removing existing holding or other functional elements, in a loosened position of a fixation screw. Like the holding elements holding the blades, the light guide holding element can be fixed to the arm by tightening the fixation screw, and may be held in a movable manner on the arm in an intermediate position of the fixation screw. Instead of a light guide, the illumination device might comprise a light source connectable to an external power source.

The illumination device may comprise a light adjustment section for adjusting the direction into which the light is emitted. The light adjustment section may be connected to the light guide holding element by a multi-axis joint, which can be configured in a similar manner as described above. Thus, the light adjustment section can be rotated freely in order to direct the light emitted by the light guide or the light source into any desired direction, but can be locked by tightening a fixation screw, which may be the same fixation screw serving for fixation of the functional element on the arm.

Examples of still further functional elements, which may be mountable on the arms in a similar manner, are stabilizers, holders for irrigation or suction tubes, additional means for holding the retractor in place, etc. The rail and/or the arms may exhibit further mounting sections for mounting such accessories.

The surgical retractor may further comprise a third arm extending substantially parallel to the rail and forming a substantially closed frame with the rail and the first and second arms. In particular, the third arm may be mounted on the first arm in a way similar to the mounting of the holding elements or further functional elements, extending substantially at right angles from the first arm towards the second arm, or vice versa. The third arm may be shaped substantially straight with a rod similar to the rod of the first or second arm as described above, to be equipped with holding elements or further functional elements. The third arm may be mountable to the first or second arm by a third arm holding element configured as an open frame for attaching the third arm to a rod of the first or second arm without removing holding or other functional elements, being fixed by tightening a fixation screw. The third arm provides additional stability and versatility to the surgical retractor.

The third arm may be mountable to one of the arms and approach or cross the other arm, or may be connectable to both first and second arms. In particular, both connections may be accomplished by third arm holding elements designed similar to the holding elements or further functional elements, or at least one of the connections may be formed by a connecting element designed differently. Connecting the third arm to both first and second arms provides additional stability to the surgical retractor.

A surgical retractor frame according to the present invention comprises an elongate rail or crossbar, a first holding arm protruding from the rail at an angle and a second arm, at least one of the arms being formed by an elongate rod, which is configured with first and second surfaces for mounting and locking at least one holding element as described above.

A holding element according to the present invention is configured to be mounted and locked on an arm of a surgical retractor, as described above.

A surgical retractor instrument set according to the present invention comprises a surgical retractor frame as described above, a multiplicity of holding elements mountable on an arm of the surgical retractor frame as described above, and a multiplicity of blades connectable to the holding elements for engaging tissue to be retracted. The surgical retractor instrument set may further comprise a tool or a set of tools for operating the fixation screws of the holding elements and/or a drive mechanism of the retractor frame. Such tools, in particular, may comprise a surgical screwdriver and/or a handle for turning the shaft of the spreading mechanism. The surgical retractor instrument set may also comprise one or a multiplicity of further functional elements or a third arm as described above.

The surgical retractor may have a small size, but provide a high force on the distal ends of the blades. Moreover, a variety of different blades can be employed with the retractor, the blades being freely movable in several degrees of freedom, but easy to lock in any desired orientation and position. The retractor thus is particularly flexibly adaptable to requirements in a large number of different surgical situations or types of surgical procedures. In particular, stability of retraction, access to the surgical site and/or view on the surgical site can be adjusted at any time according to current requirements.

In a surgical operation, the retractor usually is placed with the rail and the arms on a patient's body surface, after an elongate incision has been made and the tissues to be retracted have been separated. A multiplicity of holding elements are mounted on the first and second arms of the retractor before and/or during the operation. A multiplicity of blades is inserted into the blade holders or has been inserted before the operation or is integral with the holding elements. A minimum of 2 blades mounted in an opposing relationship is required for retraction, but in most operations, a minimum number of 4 blades is required.

The blades are introduced into the space to be spread for performing the operation and are positioned and oriented for optimal retraction. Thereafter, the blades are fixed by locking the holding elements on the arms and locking the joints by tightening the fixation screws of the holding elements. The spreading mechanism is operated for creating the space required for the surgery to be performed. The blades are thus in engagement with the tissue edges, exerting a force on the tissues for providing the space needed. If required, blades can be re-positioned and/or re-oriented by loosening the respective fixations screws, moving the blades by hand and re-tightening the fixations screws.

If required, further functional elements or a third arm can be attached to the retractor before and/or during the surgical operation.

The individual steps mentioned may be repeated or performed in a different order. In particular, at the end of the surgery, the order of steps is inverted.

The features of the invention as mentioned above and as described below apply not only in the combinations mentioned but also in other combinations or alone, without leaving the scope of the present invention.

BRIEF DESCRIPTION OF THE DRAWINGS

Further aspects of the present invention will be apparent from the figures and from the description of a particular embodiment that follows.

DETAILED DESCRIPTION OF THE INVENTION

Figure 1:
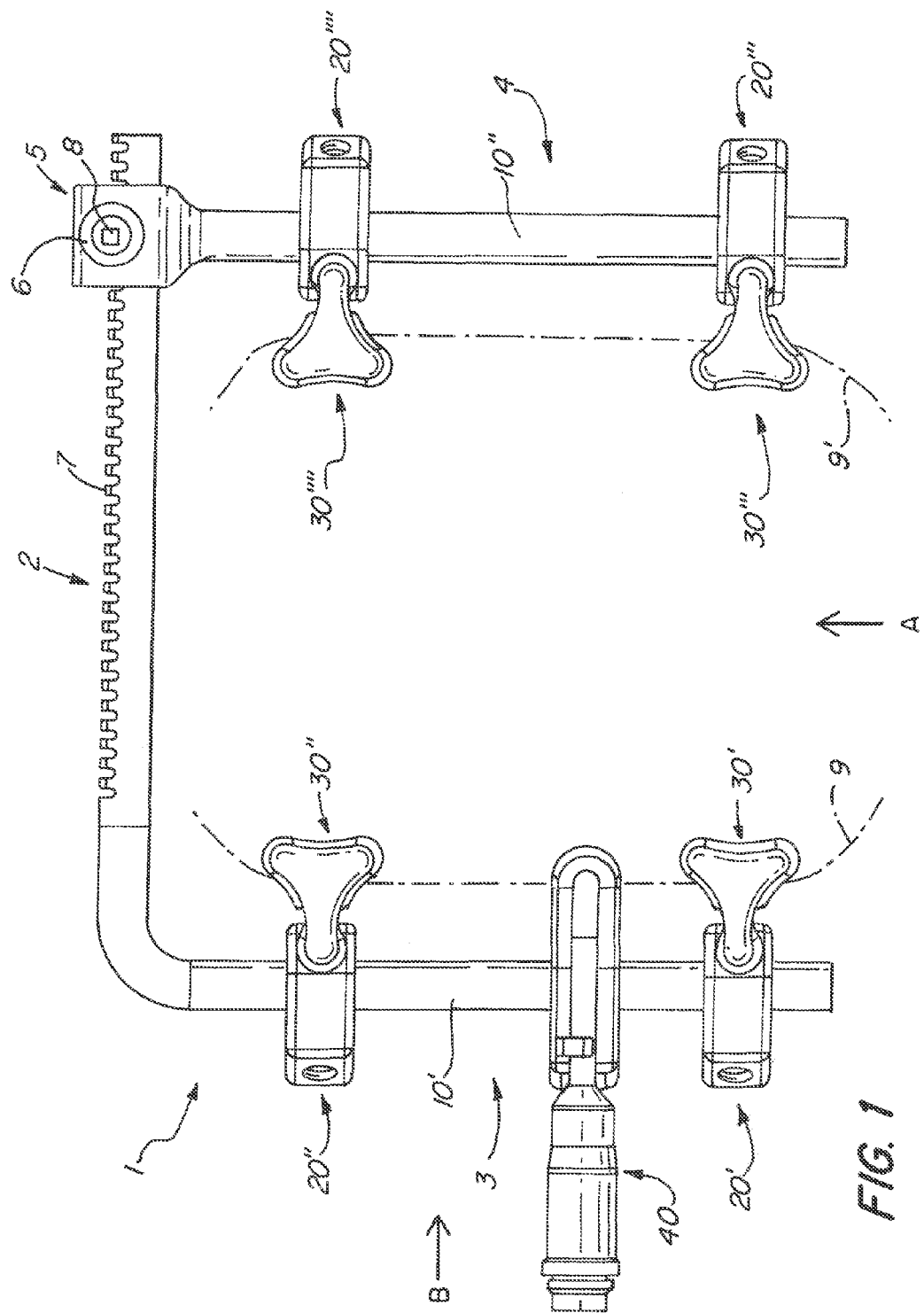
FIG. 1 shows a top view of an exemplary surgical retractor according to the present invention.

As shown in FIG. 1, an embodiment of a surgical retractor 1 comprises a rail 2, a first arm 3 and a second arm 4. The first arm 3 may be integral with the rail 2 or connected to the rail 2 in a rigid manner. The second arm 4 is connected to the rail 2 by a block 5 housing a drive mechanism 6. The drive mechanism engages with a toothed edge 7 of the rail 2 and can be operated by turning a drive shaft 8. The drive shaft 8 may exhibit a hand wheel or a detachable manipulation handle (not shown) for easier turning. The drive mechanism 6 permits adjustment of the distance between the first and second arms 3, 4. In particular, the retractor 1 can be spread or contracted by turning the drive shaft 8 in one or the other direction. Preferably, the drive mechanism 6 is configured in a self-blocking manner, i.e., the second arm 4 can be moved only by turning the drive shaft 8, but not by an external force acting upon the second arm 4 itself. Alternatively, fixation means might be provided for fixing the second arm 4 at a desired position on the rail 2.

The first arm 3 and the second arm 4 both protrude approximately at right angles from the rail, both arms being substantially parallel to each other. The first and second arms 3, 4 comprise rods 10', 10", respectively. The second arm 4 may be detachable from the rail 2. After detaching the second arm 4 from the rail, the drive mechanism 6 may be disassembled for easy cleaning.

As is further shown in FIG. 1, two holding elements 20', 20" are mounted on the first arm 3, and two further holding element 20''', 20'''' are mounted on the second arm 4. Each of the holding elements 20', 20", 20''', 20'''' holds a respective retractor blade 30', 30", 30''', 30''''. In a surgical operation, the retractor blades 30''', 30'''' engage with the tissue edge 9 and the retractor blades 30''', 30'''' engage with the tissue edge 9', the tissue edges 9, 9' being symbolically indicated in FIG. 1 by the broken lines. In order to hold the tissue edges 9, 9' apart from each other, the blades 30', 30", 30''', 30'''' are oriented such that their respective tissue gripping surfaces are directed away from the space to be held open between the tissue edges 9, 9'. Correspondingly, the holding elements 20', 20" mounted on the first arm 3 are directed substantially opposite to the holding elements 20', 20'''' mounted on the second arm 4. The holding elements 20', 20", 20'", 20"" are positioned on the respective arms 3, 4 such that a net torque arising from the counter-force exerted by the retracted tissues on the respective blades 30, 30', 30", 30'", 30"" is largely avoided. In particular, the holding elements 20', 20'" and 20", 20"" may each form a pair of two holding elements opposing each other. Further functional elements such as an illumination device 40 may be mounted on the first and/or second arms 3, 4.

Figure 2:
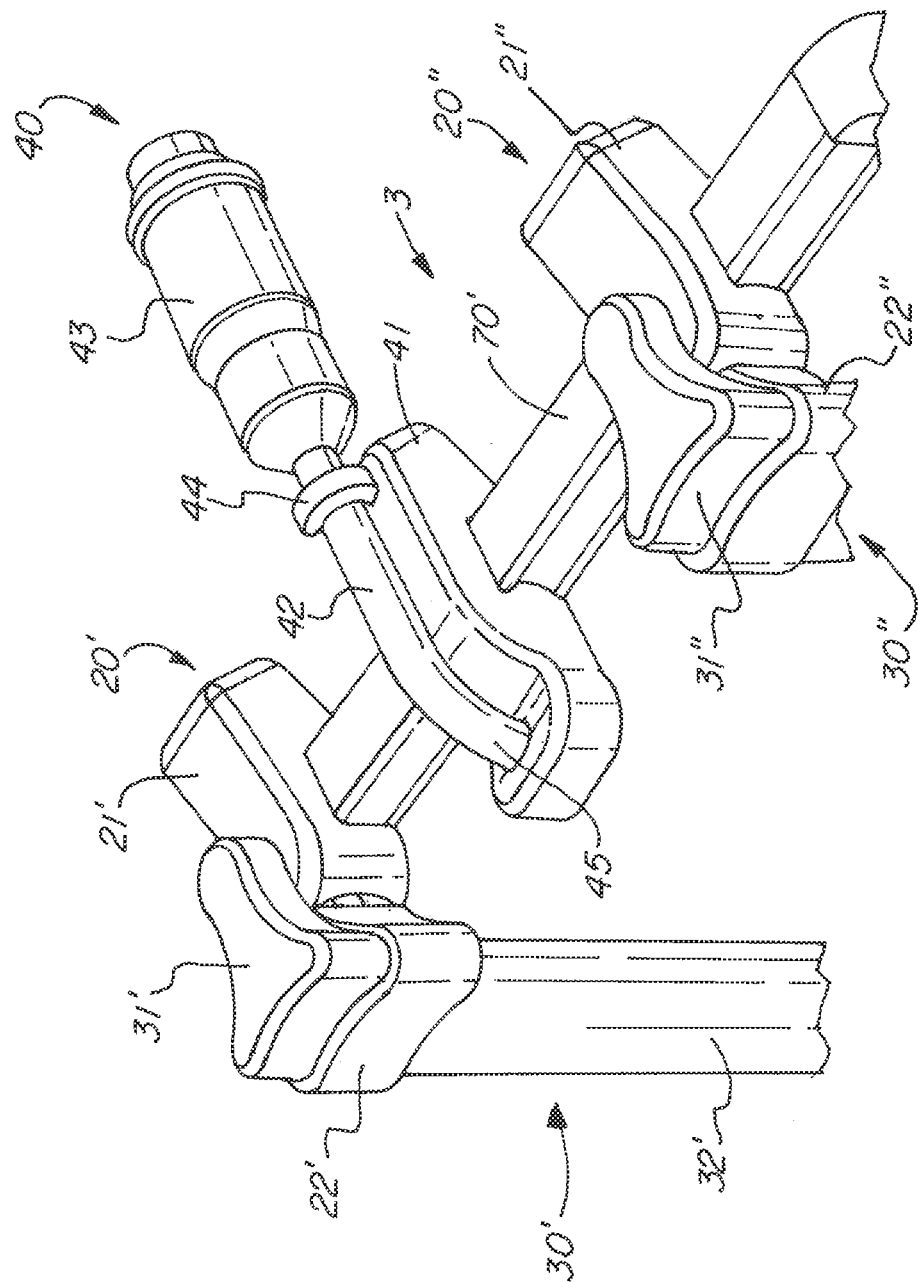
FIG. 2 shows a perspective view of one of the arms of the exemplary surgical retractor.

The first arm 3 with rod 10', holding elements 20', 20", blades 30', 30" and illumination device 40 is shown in a perspective view in FIG. 2. Each holding element 20', 20" comprises a holding element body 21', 21" and a blade holder 22', 22". Each blade 30', 30" comprises a blade head 31', 31" and a blade shaft 32', 32". The lower parts of the blades 30', 30" are not shown in FIG. 2.

The illumination device 40 comprises a light guide holder 41, a light guide 42, and a light connector 43. Light guide 42 and light connector 43 form a substantially rigid unit which can be fixed on the light guide holder by a snap-in mechanism 44. The light guide holder 41 comprises a recess into which the rod 10' is inserted to mount the light guide holder 41 on the arm 3. A light cable transmitting light from an external light source (not shown) can be connected to the light connector 43. The light connector 43 may comprise optical elements for an efficient coupling of light into the light guide 42, and for adapting the numerical aperture of the illumination light to the desired illumination characteristics. The distal end section 45 of the light guide 42 may be provided with an illumination optics and is oriented to illuminate the surgical site.

Figure 3:
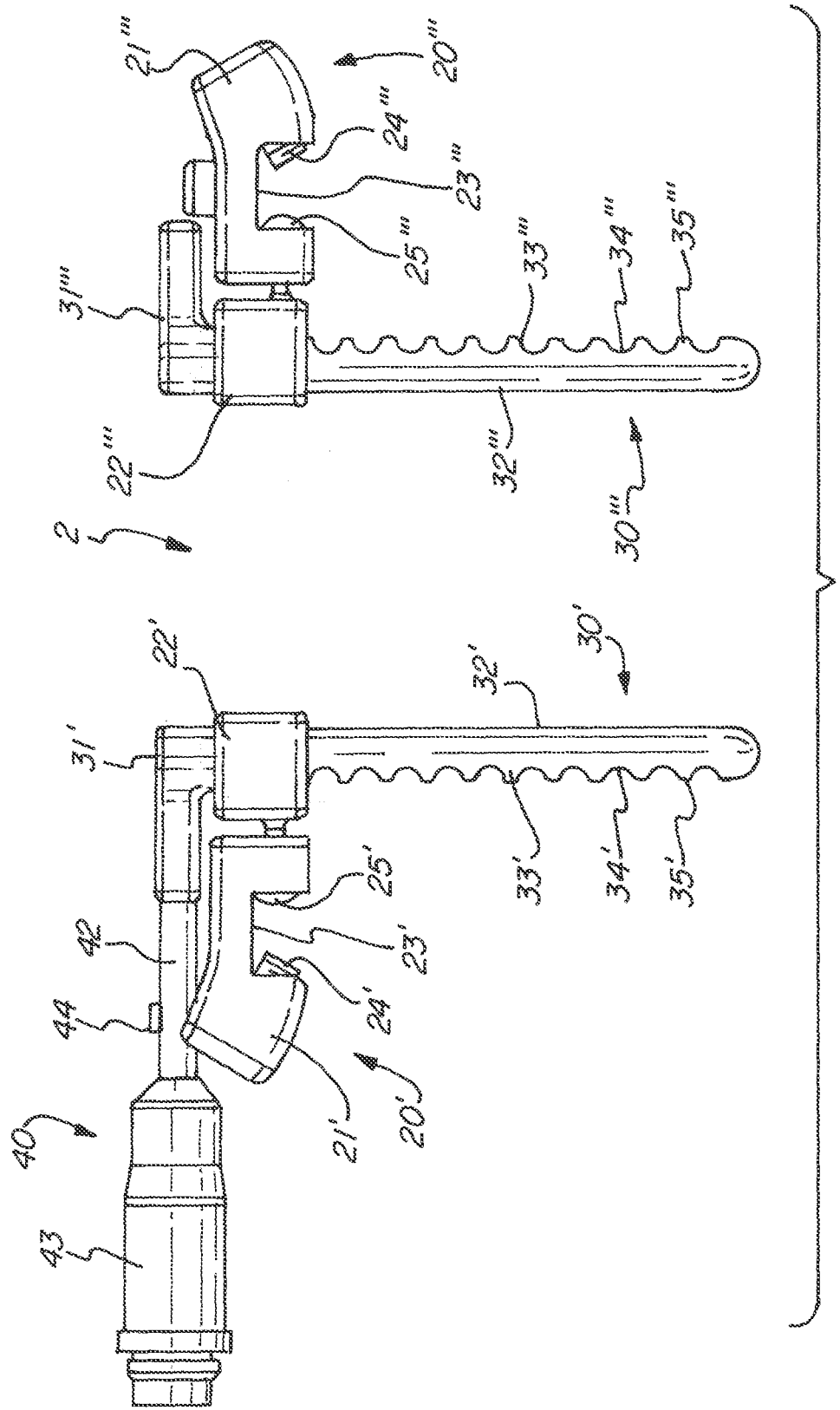
FIG. 3 shows a side view of the exemplary surgical retractor.

FIG. 3 shows a side view of the surgical retractor 1 from the direction indicated by the arrow "A" in FIG. 1. As can be seen in FIG. 3 and will be explained in detail further below, each holding element 20', 20'" comprises a body 21', 21'" and a blade holder 22', 22'" connected to the body 21', 21'" by a ball-and-socket joint. The body 21', 21'" forms an open frame with a recess 23', 23'" into which the rod of the respective arm can be inserted (not shown). The fixation screw 24', 24'" and the ball 25', 25'" of the ball-and-socket joint protrude into the recess 23', 23'" for fixing the body 21', 21'" on the rod and for locking the ball-and-socket joint against the rod. The blades 31', 31'" are held by the blade holders 22', 22'" with their respective blade gripping surfaces 33', 33'" directed away from each other. The blade gripping surfaces 33', 33'" exhibit grooves 34', 34'" and protrusions 35', 35'" for holding tissue firmly. An illumination device 40 is mounted adjacent to the holding element 20', as described above.

Figure 4:
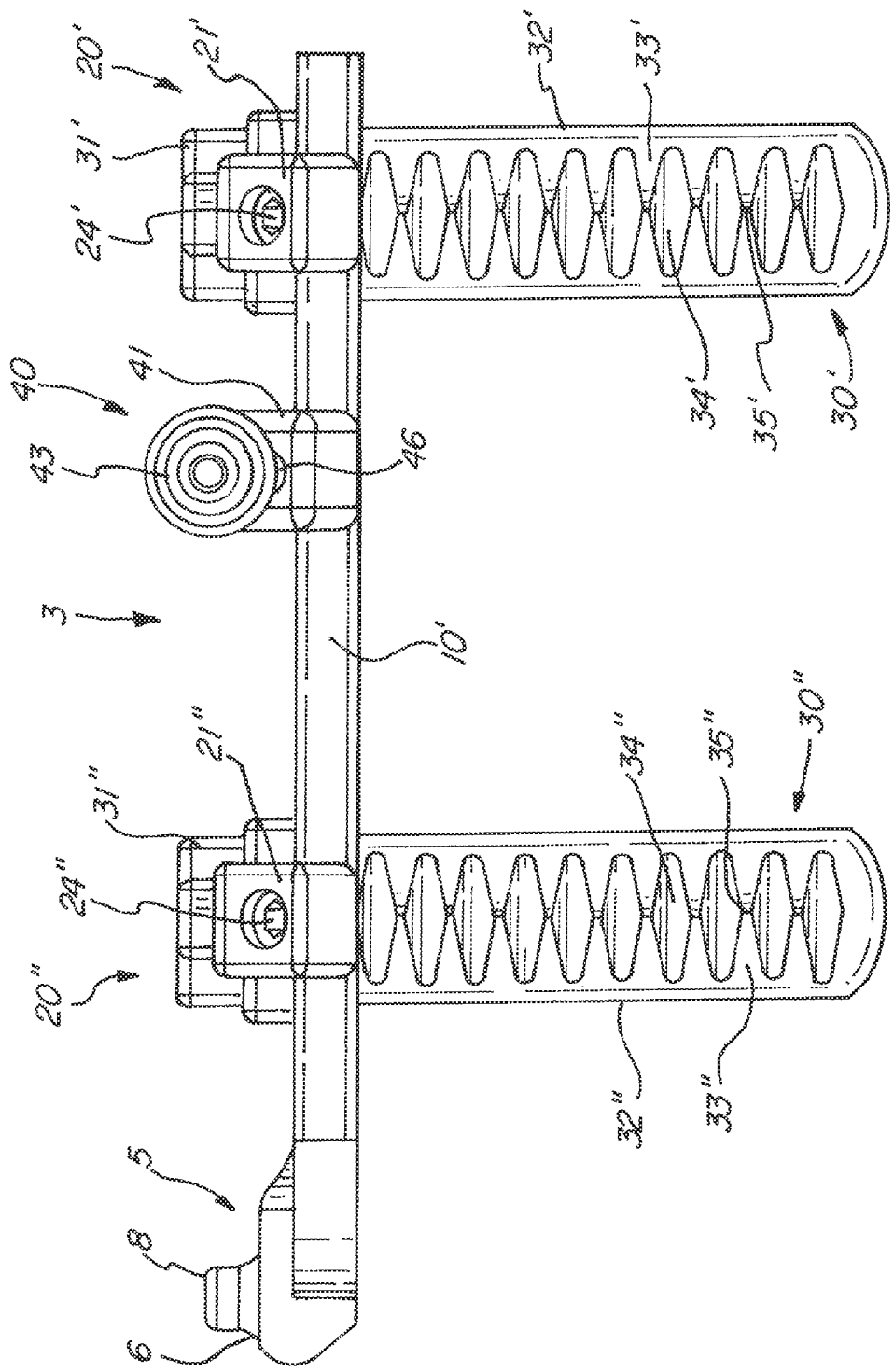
FIG. 4 shows another side view of the exemplary surgical retractor.

FIG. 4 shows a side view of the surgical retractor 1 from the direction indicated by the arrow "B" in FIG. 1. The holding elements 20', 20" are mounted on the rod 10' of the first arm 3. As can be seen in FIG. 4, the fixation screws 24', 24" exhibit a hexagonal recess for insertion of a screwdriver. The blades 30', 30" are shown in FIG. 4 with their respective tissue gripping surfaces 33', 33" which are structured with grooves 34', 34" and protrusions 35', 35". The protrusions may be ridges transverse to a longitudinal axis of blades 30', 30", respectively, or may be pyramid-shaped elevations, as indicated in FIG. 4. The illumination device 40 is mounted between the holding elements 20', 20" on the rod 10' by means of a light guide holder 41.

The light guide holder 41 can be fixed on the rod 10' by tightening a fixation screw 46 which is accessible by a corresponding tool when the light guide 42 and the light connector 43 are detached from the light guide holder 41. By tightening the fixation screw 46, the light guide holder 41 can be clamped on the rod 10'. In particular, the screw 46 acts from a first side of a recess to press the rod 10' against a second side of the recess, the latter exhibiting a cylindrical ridge fitting into a cylindrical groove of the rod 10', the latter being described below.

Figure 5:
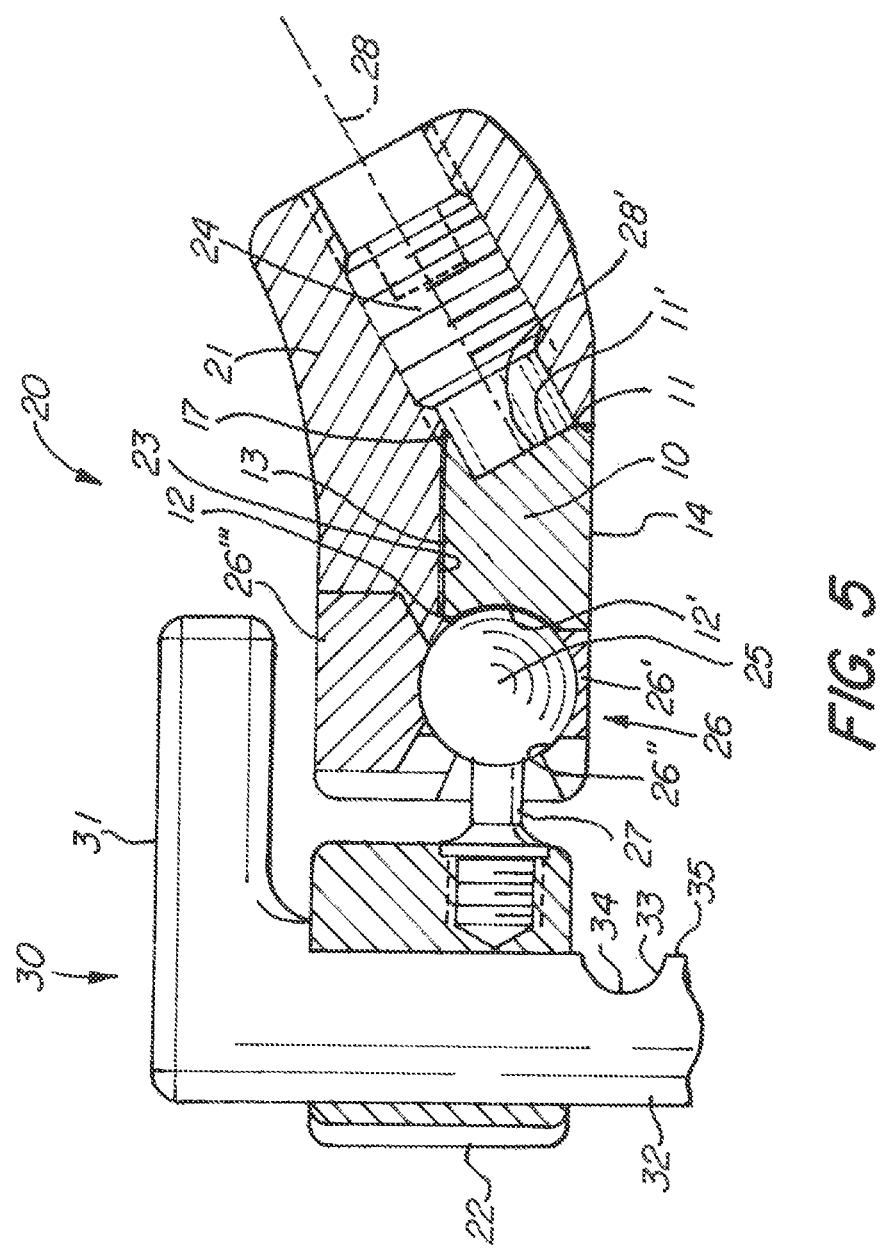
FIG. 5 shows a partial sectional view of a holding element of the exemplary surgical retractor with a retractor blade inserted.

FIG. 5 shows details of a holding element 20 in a partial sectional view. The holding element 20 comprises a holding element body 21 and a blade holder 22, the blade holder being 22 connected to the body 21 via a ball-and-socket joint 26. The ball 25 is held unreleasably within the body 21, the socket being formed by a bottom shell 26' and side members 26" being integral with the body 21, and a top shell 26'". An upper cylindrical section of the top shell 26'" fits into a corresponding bore in the body for inserting the ball 25 in the manufacturing process; the top shell 26'" is soldered or welded into the body 21 to form an integral part of it. A stud 27 of the ball is fixed to the blade holder 22, e.g. by screwing a threaded bolt of the stud 27 in the blade holder 22 (as shown in FIG. 5), and/or soldering or welding.

The body 21 comprises a recess 23 into which a rod 10 can be inserted. The rod 10, which is shown in cross-section in FIG. 5, is partly rectangular in its cross-section, having first and second surfaces 11, 12, and substantially flat top and bottom surfaces 13, 14. The top surface 13 may be parallel to the bottom surface 14. The first surface 11 has a first surface section 11' which is substantially flat, but may be inclined at an angle other than 90° to the top and bottom surfaces 11, 12. The second surface 12 has a second surface section 12' which is concave, and may, in particular, have the shape of a longitudinal section of a cylinder surface, the cylinder having a radius corresponding approximately to the radius of the ball 25. In order to facilitate introduction of the rod 10 into the recess 23, the upper edge 15, where the second surface 12 meets the top surface 13, recedes with respect to the lower edge 16, where the second surface 12 meets the bottom surface 14.

A fixation screw 24 is housed within the body 21, which abuts the first surface of the rod 10 when the rod is present in the recess 23. The fixation screw 24 has an axis 28 forming an angle to the planes defined by the top and bottom surfaces 13, 14 of the rod 10, i.e. to a plane defined by the recess 23 of the body 21. These planes may be parallel to the plane of the retractor 1 as defined by the rail 2 and the first and second arms 3, 4 (see FIG. 1). Thus, when the fixation screw 24 is operated by means of a screwdriver which is held along the screw axis 28, the screwdriver protrudes out of the plane of the surgical retractor 1.

When the holding element 20 is to be mounted on the rod 10, the fixation screw 24 is loosened to recede substantially out of the recess 23. The ball 25 still protrudes into the recess 23 by an extent depending on the play permitted by the bottom and top shells 26', 26'" and the side members 26" forming the socket of the joint. The top surface 13 has a width to permit introduction of the rod 10 from below into the recess 23. When the holding element 20 has been put on the rod 10, the fixation screw 24 is turned to protrude into the recess 23, thus inhibiting removal of the rod 10 from the recess 23, but still enabling shifting of the holding element along a longitudinal direction of the rod 10, which is perpendicular to the plane of the drawing in FIG. 5. In this position of the fixation screw 24, the ball 15 of the ball-and-socket joint 26 is still free to rotate, so that the blade 30 introduced into the blade holder 22 can be rotated to assume any desired orientation. When a the holding element 20 has a suitable position and the blade 30 has a suitable orientation, the fixation screw 24 is tightened, its tip 28' contacting the inclined first surface section 11' and thus pressing the rod 10 with its second surface section 12' against the ball 25. The ball 25 is pressed against the side members 26", forming at least one contact point with each side member 26". Thus, the ball 25 is fixed between the second surface section 12' of the rod 10 and its socket, and the rod is fixed between the ball 25 and the fixation screw 24. Fixation is improved by extended contact lines or contact areas between ball 25 and second surface section 12' and/or first surface section 11' and the tip 28' of the fixation screw 24.

As for a rigid clamping a considerable force has to be exerted by the fixation screw 24 upon the rod 10 and by the rod 10 upon the ball 25, the holding element may be reinforced by a frame 29. The frame 29 may be made of a hardened material. In total, due to the axis 28 of the screw being inclined, the holding element has an arcuate shape. The lower part of the blade 30 is not shown in FIG. 5.

Figure 6C:
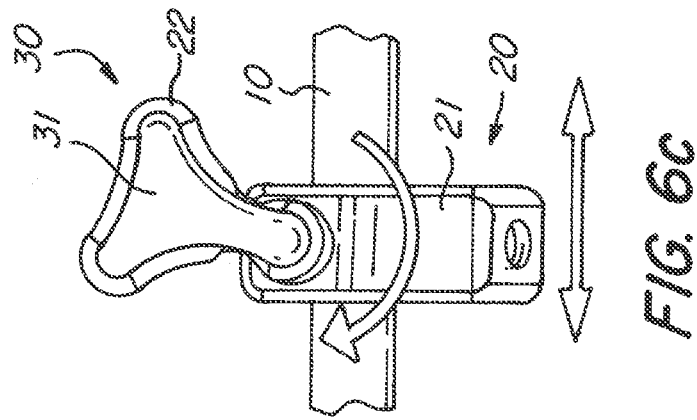
FIGS. 6A-C show various views of a holding element of the exemplary surgical retractor with a retractor blade inserted in order to demonstrate possible rotations of the blade.
Figure 6B:
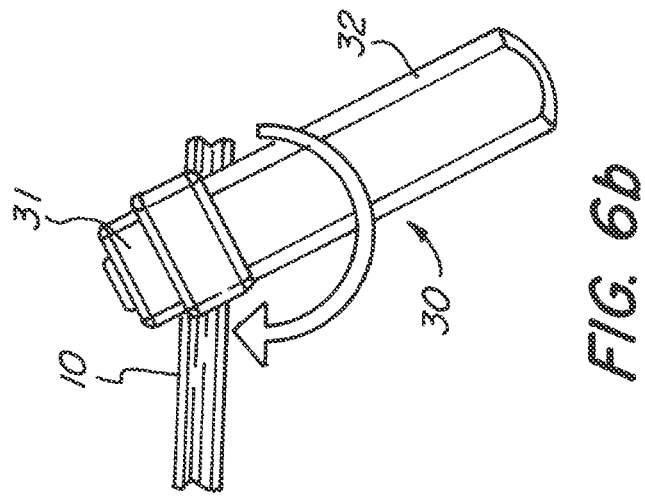
Figure 6A:
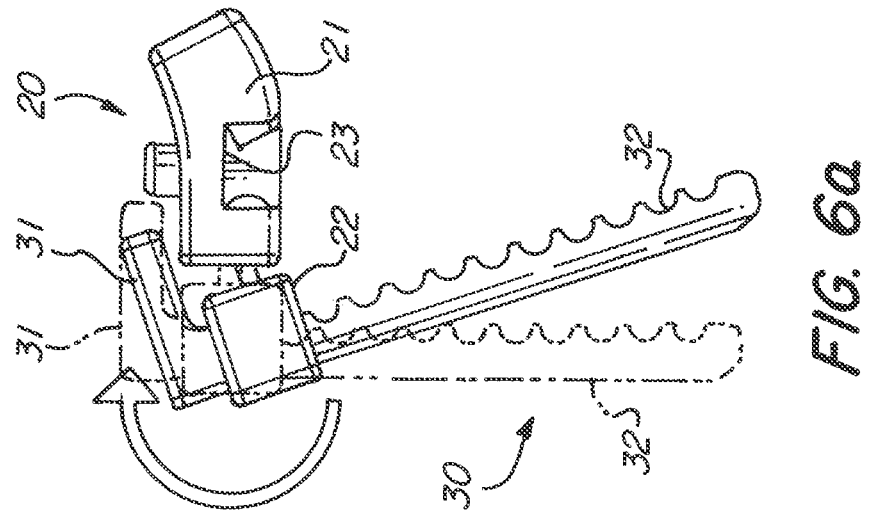

As depicted in FIG. 6*a-c*, the holding element 20 permits the blade 30 to be rotated in three rotational degrees of freedom. In particular, the blade 30 can be pivoted or swiveled about a horizontal axis parallel to a longitudinal axis of the rod 10 when inserted into the recess 23 of the body 21 of the holding element, as is indicated by the arrow in FIG. 6*a*. The blade 30 can also be pivoted with respect to a horizontal axis perpendicular to the longitudinal axis of the rod 10, as indicated by the arrow in FIG. 6*b*. Moreover, the blade can be pivoted about a vertical axis, as shown by the curved arrow in FIG. 6*c*. Finally, the holding element can be shifted along the rod 10 as indicated by the straight arrow in FIG. 6*c*, thus shifting the blade 30 in a self-parallel manner.

Figure 7:
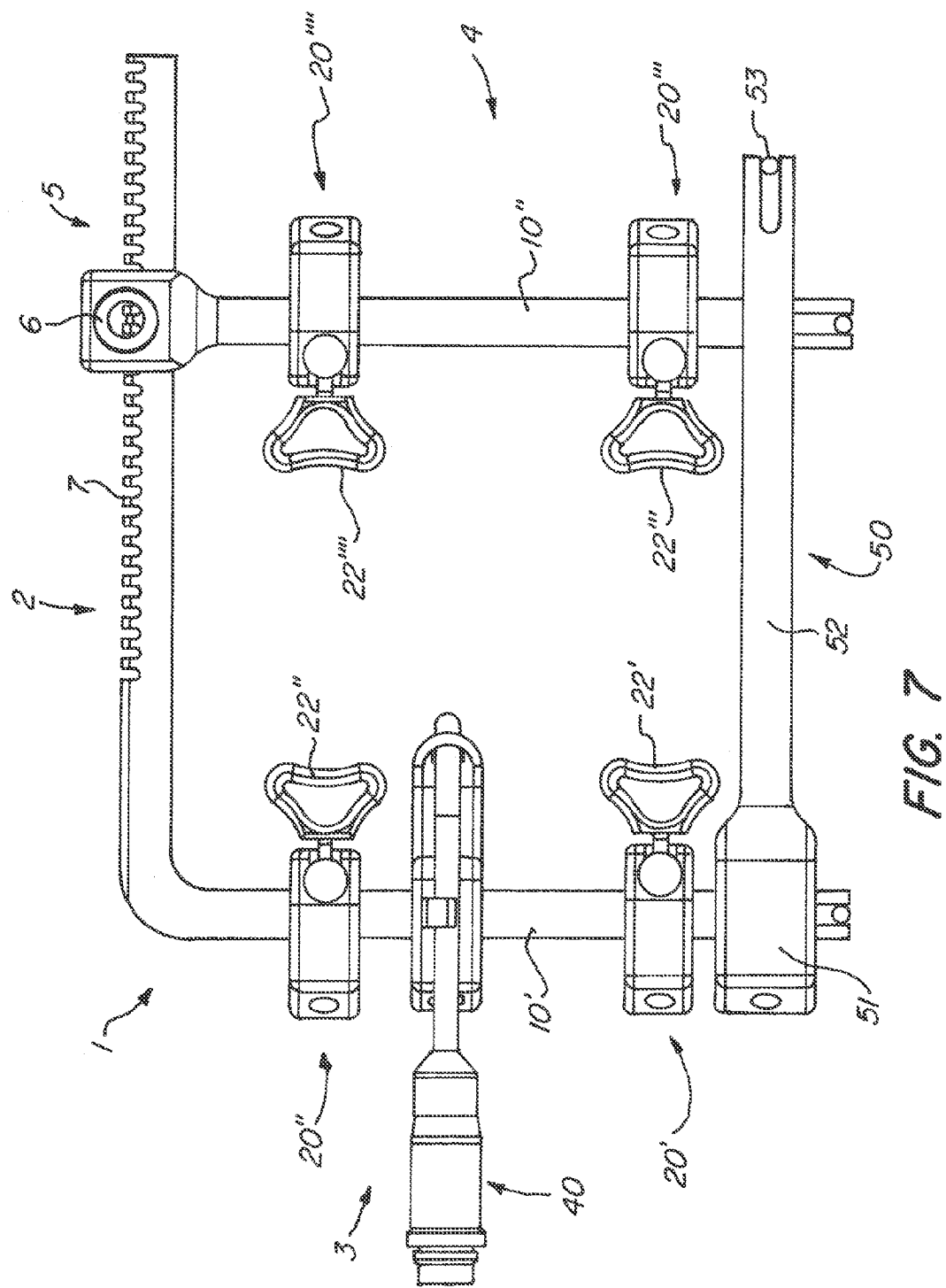
FIG. 7 shows a top view of an exemplary surgical retractor including a third arm.

As indicated in FIG. 7, the surgical retractor 1 may further comprise a third arm 50 extending parallel to the rail 2 and being mounted on one of the arms 3, 4. The third arm comprises a third arm holding element 51 and a rod 52. The third arm holding element 51 is mountable on the rod 10', 10" of the first or second arms 3, 4 in a similar way as the illumination device 40. In the configuration shown in FIG. 7, the rod 52 of the third arm 50 crosses over the second arm 4 in order to make the retractor 1 form a closed frame, but permitting free adjustment of the distance between the first and second arms 3, 4 by operating the drive mechanism 6 of the second arm 4. For enhanced stiffness, the third arm 4 may be connectable to the second arm 4 (not shown). The rod 52 is arranged parallel to the rail 2 but slightly elevated, a bottom surface of the rod 52 coinciding with the plane formed by the top surfaces of the rods 10', 10" of the first and second arms 3, 4. The third arm holding element 51 provides for the corresponding elevation of the rod 52.

Further holding elements or further functional elements can be mounted on the rod 52 of the third arm 50. As indicated in FIG. 7, the free end of the rod 52 may be equipped with a resilient ratchet mechanism, e.g. a spring-born ball 53. In this way, unintentional loss of a holding or further functional element can be avoided when the fixation screw of the element is in a position to permit translation along the rod, but not removal from the rod. The free ends of the rods 10', 10" of the first and second arms 3, 4 may exhibit similar mechanisms.

Reference numerals not explicitly mentioned in the description of one of the figures have the same meaning as in the other figures.

What is claimed is:

1. Surgical retractor comprising a rail, a first arm protruding from the rail at an angle, a second arm being movably mounted on the rail and extending substantially parallel to the first arm, and a multiplicity of holding elements mounted on the first and second arms, a holding element comprising a joint for pivotably holding a blade for engaging tissue to be retracted, characterized in that the joint is a multi-axis joint, characterized in that the holding element comprises an aperture for inserting a rod of an arm for mounting the holding element on the arm and fixation means comprising a fixation screw to act upon the rod for fixing the holding element on the arm, characterized in that a movable member of the multi-axis joint is arranged on one side of the aperture, such that one surface of the rod is pressed against the movable member of the multi-axis joint by operation of the fixation screw.

2. Surgical retractor according to claim 1, characterized in that the holding element comprises a blade holder for holding at least one blade and a holding element body for connecting the holding element on an arm, the two-axis joint connecting the blade holder to the holding element body.

3. Surgical retractor according to claim 1, characterized in that the at least one blade can be freely inserted into the blade holder for engaging tissue to be retracted and is fixed within the blade holder by a force exerted by the retracted tissue on the blade.

4. Surgical retractor according to claim 1, characterized in that the multi-axis joint is a spherical joint.

5. Surgical retractor comprising a rail, a first arm protruding from the rail at an angle, a second arm being movably mounted on the rail and extending substantially parallel to the first arm, and a multiplicity of holding elements mounted on the first and second arms, a holding element comprising a joint for pivotably holding a blade for engaging tissue to be retracted, characterized in that the joint is a multi-axis joint, characterized in that the holding element comprises fixation means for blocking the multi-axis joint.

6. Surgical retractor according to claim 1, characterized in that the retractor further comprises a third arm extending substantially parallel to the rail and forming a substantially closed frame with the rail and the first and second arms.

7. Surgical retractor according to claim 5, characterized in that the fixation means comprises a fixation screw acting upon a movable member of the multi-axis joint.

8. Surgical retractor comprising a rail, a first arm protruding from the rail at an angle, a second arm being movably mounted on the rail and extending substantially parallel to the first arm, and a multiplicity of holding elements mounted on the first and second arms, a holding element comprising a joint for pivotably holding a blade for engaging tissue to be retracted, characterized in that the joint is a multi-axis joint, characterized in that the holding element comprises an aperture for inserting a rod of an arm for mounting the holding element on the arm and that the holding element comprises fixation means for fixing the holding element on the arm.

9. Surgical retractor according to claim 8, characterized in that the aperture is a recess for laterally inserting a rod of an arm.

10. Surgical retractor according to claim 9, characterized in that a longitudinal axis of the fixation screw is oblique with respect to a plane formed by the arm on which the holding element is mounted and the rail in a portion adjacent to the arm.

11. Surgical retractor according to claim 9, characterized in that a section of the first surface of the rod is substantially perpendicular to the axis of the fixation screw.

12. Surgical retractor according to claim 8, characterized in that the fixation means comprises a fixation screw situated on a first side of the aperture to act upon a first surface of the rod for fixing the holding element on the arm.

13. Surgical retractor according to claim 12, characterized in that a movable member of the multi-axis joint is arranged on a second side of the aperture, such that a second surface of the rod can be pressed against a surface of the movable member of the multi-axis joint by operating the fixation screw.

14. Surgical retractor according to claim 13, characterized in that in the movable member is the ball of a ball-and-socket joint and that the socket is rigidly connected to the holding element.

15. Surgical retractor according to claim 14, characterized in that the second surface of the rod comprises a longitudinal cylindrical groove such that the surface of the ball forms a line of contact with the second surface of the rod when being pressed against the rod.

* * * * *